US00PP13578P2

(12) United States Plant Patent
Fleming et al.

(10) Patent No.: US PP13,578 P2
(45) Date of Patent: Feb. 18, 2003

(54) DIANTHUS PLANT NAMED 'PIXIE'

(75) Inventors: David W. Fleming, Lincoln, NE (US); Gretchen A. Zwetzig, Lincoln, NE (US)

(73) Assignee: Board of Regents of the University of Nebraska, Lincoln, NE (US)

( * ) Notice: Subject to any disclaimer, the term of this patent is extended or adjusted under 35 U.S.C. 154(b) by 0 days.

(21) Appl. No.: 10/004,778

(22) Filed: Dec. 7, 2001

(51) Int. Cl.[7] ..... A01H 5/00

(52) U.S. Cl. ..... Plt./282

(58) Field of Search ..... Plt./282, 281, 283

*Primary Examiner*—Bruce R. Campell
*Assistant Examiner*—Anne Marie Grünberg
(74) *Attorney, Agent, or Firm*—C. A. Whealy

(57) ABSTRACT

A distinct cultivar of Dianthus plant named 'Pixie', characterized by its compact, mounded and low-growing plant habit; freely basal branching habit; blue green-colored foliage; numerous red purple-colored flowers with lighter red purple spots and margins; and hardiness rating to USDA zone 4.

1 Drawing Sheet

BOTANICAL CLASSIFICATION/CULTIVAR DESIGNATION

*Dianthus gratianopolitanus* cultivar Pixie.

BACKGROUND OF THE INVENTION

The present invention relates to a new and distinct cultivar of Dianthus plant, botanically known as *Dianthus gratianopolitanus* and hereinafter referred to by the name 'Pixie'.

The new cultivar is a product of a planned breeding program conducted by the Inventors in Lincoln, Nebr. The objective of the breeding program is to create new Dianthus cultivars having compact plant habit, hardiness, good garden performance, and attractive flower coloration.

The new Dianthus originated from a self-pollination made by the Inventors in 1990, in Lincoln, Nebr., of the Dianthus cultivar Spotty, not patented. The new Dianthus was discovered and selected by the Inventors as a single flowering plant within the progeny of the stated self-pollination grown in a controlled environment in Lincoln, Nebr. in 1990. The selection of this plant was based on its compact plant habit and attractive flower coloration.

Asexual reproduction of the new Dianthus by vegetative stem cuttings taken in a controlled environment in Lincoln, Nebr., since 1993, has shown that the unique features of this new Dianthus are stable and reproduced true to type in successive generations.

SUMMARY OF THE INVENTION

The cultivar Pixie has not been observed under all possible environmental conditions. The phenotype may vary somewhat with variations in environment such as temperature, daylength, light intensity, and water and nutritional status without, however, any variance in genotype.

The following traits have been repeatedly observed and are determined to be the unique characteristics of 'Pixie'. These characteristics in combination distinguish 'Pixie' as a new and distinct cultivar:

1. Compact, mounded and low-growing plant habit.
2. Freely basal branching habit.
3. Blue green-colored foliage.

4. Numerous red purple-colored flowers with lighter red purple spots and lighter red purple margins.
5. Hardy to USDA zone 4.

Plants of the new Dianthus can be compared to plants of the parent, the cultivar Spotty. In side-by-side comparisons conducted in Lincoln, Nebr., plants of the new Dianthus and the cultivar Spotty differed in the following characteristics:

1. Plants of the new Dianthus had blue green-colored foliage whereas plants of the cultivar Spotty had gray green-colored foliage.
2. Plants of the new Dianthus had less pronounced spots on the flowers than plants of the cultivar Spotty.
3. Flowers of plants of the new Dianthus were red purple in color whereas flowers of plants of the cultivar Spotty were red in color.
4. Plants of the new Dianthus were hardier than plants of the cultivar Spotty.

Plants of the new Dianthus can be compared to plants of the cultivar Painted Beauty, not patented. In side-by-side comparisons conducted in Lincoln, Nebr., plants of the new Dianthus and the cultivar Painted Beauty differed in the following characteristics:

1. Plants of the new Dianthus had blue green-colored foliage whereas plants of the cultivar Painted Beauty had gray green-colored foliage.
2. Plants of the new Dianthus had less pronounced spots on the flowers than plants of the cultivar Painted Beauty.
3. Flowers of plants of the new Dianthus were lighter in color than flowers of plants of the cultivar Painted Beauty.

Plants of the new Dianthus can also be compared to plants of the cultivar Frosty Fire, not patented. In side-by-side comparisons conducted in Lincoln, Nebr., plants of the new Dianthus and the cultivar Frosty Fire differed in the following characteristics:

1. Petals of plants of the new Dianthus were more overlapping than petals of plants of the cultivar Frosty Fire.
2. Flowers of plants of the new Dianthus were red purple in color whereas flowers of plants of the cultivar Frosty Fire were red in color.

BRIEF DESCRIPTION OF THE PHOTOGRAPH

The accompanying colored photograph illustrates the overall appearance of the new Dianthus, showing the colors as true as it is reasonably possible to obtain in colored reproductions of this type. Colors in the photograph may differ slightly from the color values cited in the detailed botanical description which accurately describe the colors of the new Dianthus.

The photograph comprises a side perspective view of a one year-old flowering plant of 'Pixie' grown in a container.

DETAILED BOTANICAL DESCRIPTION

In the following description, color references are made to The Royal Horticultural Society Colour Chart, 1995 edition, except where general terms of ordinary dictionary significance are used. The aforementioned photograph, following observations and measurements describe plants grown in Lancaster, Pa. during the spring and summer outdoors under full sunlight and cultural conditions which approximate commercial practice. Measurements and numerical values represent averages of one year-old flowering plants grown in 1-liter containers.

Botanical classification: *Dianthus gratianopolitanus* cultivar Pixie.

Parentage: Self-pollination of *Dianthus gratianopolitanus* cultivar Spotty, not patented.

Propagation:

*Type.*—By vegetative stem cuttings.

*Time to initiate roots.*—Summer: About 10 days at 75° F. Winter: About 14 days at 75° F.

*Time to produce a rooted cutting.*—Summer: About 17 days at 75° F. Winter: About 21 days at 75° F.

*Root description.*—Fine, fibrous.

Plant description:

*Plant habit.*—Compact, mounded and low-growing.

*Growth habit.*—Freely basal branching; when pinched, lateral shoots potentially develop at every node.

*Plant height.*—About 23 cm.

*Plant width.*—About 45 cm.

*Lateral branch description.*—Length: About 31 cm. Diameter: About 1.5 mm. Internode length: About 7.5 cm. Aspect: Upright to outwardly spreading to trailing. Strength: Strong, but flexible. Texture: Glabrous, covered with waxy bloom. Color: 145A to 145B; overlain with anthocyanin, 187A; covered with waxy bloom, close to 156D.

*Foliage description.*—Arrangement: Leaves simple; symmetrical; abundant; opposite; sessile and decurrent. Length: About 6.5 cm. Width: About 3 mm. Shape: Linear. Apex: Sharply acute. Margin: Ciliate. Texture, upper and lower surfaces: Glabrous, covered with waxy bloom. Venation pattern: Parallel, linear. Color: Young and mature foliage, upper and lower surfaces: 146A overlain with bloom, 136C, giving an overall blue green tonality. Venation, upper and lower surfaces: Same as lamina.

Flowering description:

*Appearance.*—Single rounded flowers that face upright. One flower per lateral branch; freely flowering, usually about 30 to 40 flowers per plant throughout the flowering season.

*Flowering response.*—Plants flower from spring through early summer in Lincoln, Nebr.; during this period, flowering is continuous.

*Postproduction longevity.*—Flowers last about 3 to 7 days on the plant. Flowers persistent.

*Fragrance.*—Moderately fragrant; spicy, clove-like.

*Flower size.*—Diameter: About 2.8 cm. Depth (height): About 2.6 cm.

*Flower buds.*—Length: About 2 cm. Diameter: About 4 mm. Shape: Tubular, elongated. Color: 144A.

*Petals.*—Quantity: Five in a single whorl. Length: From base: About 3.8 cm. Beyond calyx tube: About 1.4 cm. Width: At base: About 1 mm. At calyx tube apex: About 4 mm. Beyond calyx tube: About 1.3 cm. Shape: Roughly spatulate or fan-shaped, tapering towards base. Apex: Rounded, emarginate. Base: Attenuate. Margin: Emarginate giving a fringed appearance. Texture: Velvety; sparse pubescence on upper surface; lower surface, glabrous. Color: When opening, upper surface: 61A; dappled center, 70A to 70B; towards base, 145C to 145D; margin, 70A to 70B. When opening, lower surface: 75B to 75C; towards base, 145C to 145D; margin, 70A to 70B. Fully opened, upper surface: 61A; dappled center, close to 70B to 70C; towards base, 145C to 145D; margin, 70B to 70C; with subsequent development, color becomes more intense than 61A. Fully opened, lower surface: 75C to 75D; towards base, 145C to 145D; margin, 70D.

*Sepals.*—Quantity/arrangement: Five per flower fused into a calyx tube. Calyx length: About 2.2 cm. Calyx diameter: About 5 mm. Calyx shape: Tubular, elongate. Apex: Acute. Texture: Smooth, glabrous. Color: Inner surface: 146A overlain with anthocyanin, close to 187A at apices and towards base. Outer surface: 144A.

*Peduncles.*—Length: About 2.8 cm. Diameter: About 1 mm. Aspect: Upright. Strength: Strong. Color: 145A to 145B; slightly overlain with anthocyanin, 187A; covered with waxy bloom, close to 156D.

*Reproductive organs.*—Androecium: Stamen number: About 10. Filament length: About 8 mm. Filament diameter: Less than 1 mm. Filament color: Close to 155D. Anther size: About 1 mm by less than 1 mm. Anther shape: Roughly oblong. Anther color: Close to 10C. Pollen: Scarce. Pollen color: Close to 10C. Gynoecium: Pistil quantity: One. Pistil length: About 2.1 cm. Pistil diameter: Less than 1 mm. Style length: About 6 mm. Style diameter: Less than 1 mm. Style color: Close to 155D. Stigma shape: Linear, recurved. Stigma color: Close to 72A. Ovary color: 144A to 144B.

*Fruit.*—Length: About 2.7 cm. Diameter: About 5 mm. Texture: Smooth with four longitudinal sutures. Color: Close to 146A.

*Seed.*—Quantity: About 25 per fruit. Length: About 3 mm. Diameter: About 2.5 mm. Shape: Roughly ovate to oblong, flattened. Color: Close to 164B to 164A with development.

Disease/pest resistance: Plants of the new Dianthus have not been observed to be resistant to pathogens nor pests common to Dianthus.

Hardiness: Plants of the Dianthus have been observed to be hardy to USDA zone 4.

It is claimed:

1. A new and distinct cultivar of Dianthus plant named 'Pixie', as illustrated and described.

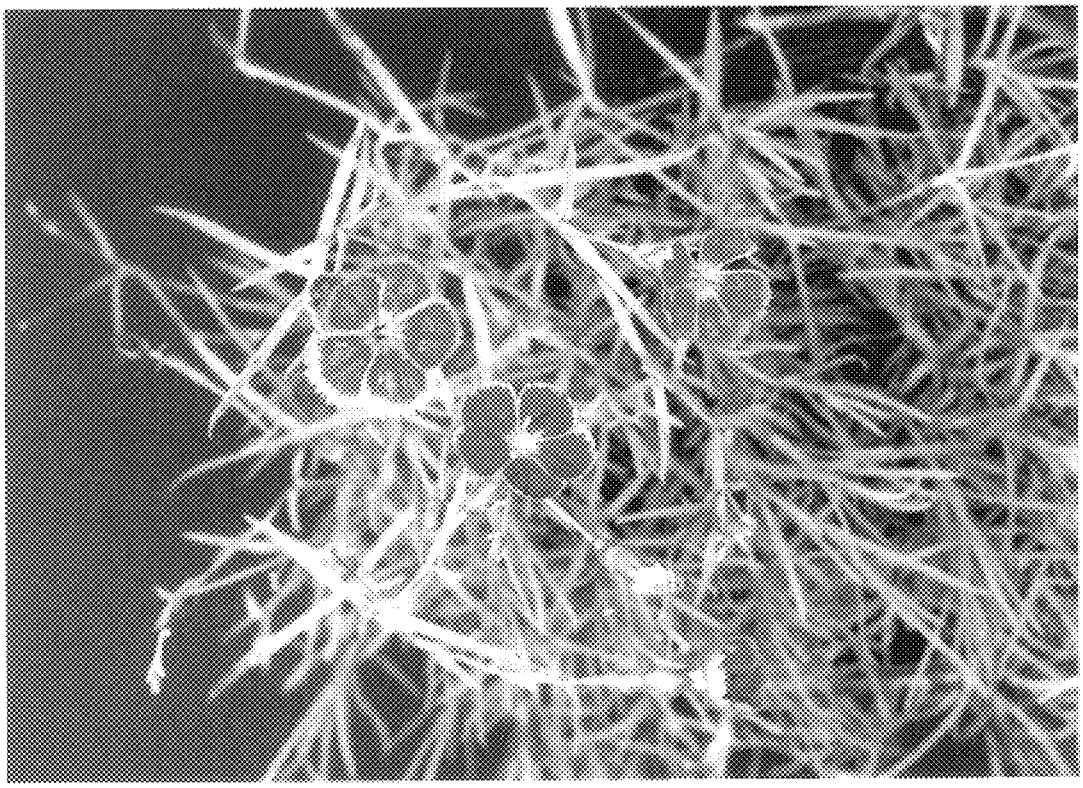

* * * * *